(12) United States Patent
Hsieh

(10) Patent No.: US 10,376,375 B2
(45) Date of Patent: Aug. 13, 2019

(54) SUPPORTING MEMBER FOR IMPLANTING INTO VERTEBRA AND IMPLANTING SYSTEM AND METHOD USING THE SAME

(71) Applicant: Jui-Yang Hsieh, Taipei (TW)

(72) Inventor: Jui-Yang Hsieh, Taipei (TW)

( * ) Notice: Subject to any disclaimer, the term of this patent is extended or adjusted under 35 U.S.C. 154(b) by 250 days.

(21) Appl. No.: 15/493,752

(22) Filed: Apr. 21, 2017

(65) Prior Publication Data

US 2017/0304067 A1    Oct. 26, 2017

(30) Foreign Application Priority Data

Apr. 22, 2016 (TW) .............................. 105205769 A

(51) Int. Cl.
*A61F 2/44* (2006.01)
*A61F 2/46* (2006.01)
*A61F 2/30* (2006.01)

(52) U.S. Cl.
CPC .......... *A61F 2/442* (2013.01); *A61F 2/30771* (2013.01); *A61F 2/4455* (2013.01); *A61F 2/4601* (2013.01); *A61F 2/4611* (2013.01); *A61F 2002/30377* (2013.01); *A61F 2002/30593* (2013.01); *A61F 2002/30604* (2013.01); *A61F 2002/30904* (2013.01); *A61F 2002/4435* (2013.01)

(58) Field of Classification Search
CPC .... A61F 2/442; A61F 2/30771; A61F 2/4601; A61F 2/4455
See application file for complete search history.

(56) References Cited

U.S. PATENT DOCUMENTS

2015/0045894 A1* 2/2015 Hawkins ............... A61F 2/4455
623/17.16

* cited by examiner

*Primary Examiner* — Christian A Sevilla
(74) *Attorney, Agent, or Firm* — Birch, Stewart, Kolasch & Birch, LLP

(57) ABSTRACT

The present invention provides a supporting member for implanting into a vertebra of a subject, including: a hollow body including an upper surface and a lower surface opposite the upper surface; a first guiding part formed on the upper surface; a second guiding part corresponding to the first guiding part and formed on the lower surface; a first engaging part formed on the upper surface; and a second engaging part corresponding to the first engaging part and formed on the lower surface; wherein the second guiding part extends out an extending part from a side of the hollow body, and the extending part is configured to be slidably coupled to a first guiding part of another supporting member sliding to the lower surface of the supporting member, as a result two supporting members are slidably coupled to each other and engaged to each other. According to the invention, one single supporting member can be implanted into a vertebra of a subject, or two or more supporting members can be in sequence introduced into a vertebra of a subject and combined together therein.

20 Claims, 6 Drawing Sheets

US 10,376,375 B2

SUPPORTING MEMBER FOR IMPLANTING INTO VERTEBRA AND IMPLANTING SYSTEM AND METHOD USING THE SAME

RELATED APPLICATIONS

This application claims the benefit of Taiwanese Patent Application No. 105205769, filed on Apr. 22, 2016, the entire content of which is incorporated herein by reference.

FIELD OF THE INVENTION

The present invention relates to a supporting member for implanting into a vertebra, more particularly to multiple supporting members combinable in a vertebra. The present invention also relates to an intra-vertebral implanting system and method using the one or more supporting members.

BACKGROUND OF THE INVENTION

People diagnosed with osteoporosis are likely to lose so much bone tissue that they end up with a vertebral compression fracture. Most vertebral compression fractures heal in months. However, osteoporosis patients in convalescence are predisposed to back pain and compression neuropathy and are to the detriment of physical ability; as a result, they become bedridden and even suffer from complications, such as bedsores, pneumonia, and urinary tract infections. Sometimes osteoporosis-induced vertebral compression fractures do not heal, and the unhealed fractures are accompanied by persistent pain, leading to spinal instability and even lordosis, kyphosis, scoliosis, and deformation of vertebrae; eventually, adjacent vertebrae undergo vertebral compression fractures multiplied by a domino effect.

Both open posterior vertebral fixation and spine fusion surgery entail driving screws into a vertebrae to lend support thereto. However, screws driven into osteoporosis patients' vertebrae are likely to loosen. To solve this problem, more screws are driven into more vertebrae of an osteoporosis patient than a non-osteoporosis patient; as a result, prolonged surgery and massive bleeding lead to more complications, such as cardiopulmonary failure and infections.

Minimally invasive percutaneous vertebroplasty involves introducing bone cement into a fractured vertebra. The bone cement is introduced into the fractured vertebra by using a bone puncture needle guided by x-ray imaging while being admitted into a small wound and then passed through the pedicle before it reaches the fractured vertebra. The purpose of introducing bone cement into a fractured vertebra is to support an otherwise collapsed vertebra and achieve analgesia. Nonetheless, minimally invasive percutaneous vertebroplasty cannot correct a deformed vertebra. By contrast, minimally invasive percutaneous kyphoplasty, which restores the height of a fractured vertebra with an inflatable balloon, entails putting the inflatable balloon in the fractured vertebra, removing the balloon from the fractured vertebra, and introducing polymethylmethacrylate into the cavity created as a result of distension of the balloon, thereby correcting the collapsed, deformed vertebra in part.

A recently developed technique for the sped-up healing of a vertebra that suffers from compression fracture involves implanting a filler into the vertebra through the pedicle. However, when the required filler is too large, it is likely to injure peripheral nerves while passing through the pedicle. But if the implanted filler is too small, it cannot support the vertebra.

SUMMARY OF THE INVENTION

In view of the aforesaid drawbacks of the prior art pertaining to the treatment of vertebral compression fractures, the present invention provides a combinable supporting member for implanting into a vertebra, comprising:

a hollow-cored portion having an upper surface and a lower surface opposing the upper surface;
a first guide portion formed on the upper surface;
a second guide portion corresponding in position to the first guide portion and formed on the lower surface;
a first engaging portion formed on the upper surface; and
a second engaging portion corresponding in position to the first engaging portion and formed on the lower surface,
wherein the second guide portion extends outward from the hollow-cored portion, along a first axis, to form an extending portion, to which another supporting member is slidably coupled along the first axis.

In particular, such another supporting member, guided by the extending portion, slides and moves to the lower surface of the supporting member. In more particular, the first guide portion of a second supporting member and the second guide portion of a first supporting member are slidably coupled to each other, and the first and second engaging portions of the two supporting members are engaged with each other. According to the present invention, a single supporting member can be implanted into the vertebra; alternatively, two or more supporting members can be implanted into the vertebra one by one and then combined therein.

A medical professional can implant a single supporting member into a vertebra of a patient as needed or implant multiple supporting members (two or more supporting members) into the vertebra of the patient one by one. Each supporting member can be made in a small size suitable to be implanted into the vertebra and then be engaged with another supporting member which has been implanted in the vertebra. Therefore, the supporting member for implanting into a vertebra according to the present invention overcomes drawbacks of the prior art (for example, implanting a single filler into a collapsed vertebra comes with the likelihood of injuring peripheral nerves while the single filler is penetrating the pedicle of the vertebra, and implanting a single filler of a wrong size into a collapsed vertebra provides no support thereto).

In some embodiments, the hollow-cored portion of the supporting member is in a cubic shape.

In some embodiments, at least one opening is disposed on a lateral side of the hollow-cored portion.

In some embodiments, a screw hole is disposed on a lateral side of the hollow-cored portion.

In some embodiments, the first guide portion comprises a first proximal end extending to a distal end along the first axis.

In some embodiments, the first guide portion comprises a recess that comprises a first proximal end extending to a distal end along the first axis, and the second guide portion comprises a rib extending outward from a lateral surface of the hollow-cored portion of the supporting member, along the first axis, to form an extending shaft as the extending portion.

In some embodiments, the first engaging portion is formed on two sides of the first guide portion, and the second engaging portion is formed on two sides of the second guide portion.

In some embodiments, the first engaging portion comprises a plurality of teeth each comprising a first oblique surface and a second oblique surface with a steeper slope than the first oblique surface, and the second engaging portion comprises a plurality of teeth each comprising a third oblique surface and a fourth oblique surface with a steeper slope than the third oblique surface.

In some embodiments, the supporting member is made of a metal, a polymer plastic, or a biodegradable material.

The present invention also provides an intra-vertebral implanting system (or kit) comprising one or more supporting members as described herein.

Specifically, the intra-vertebral implanting system of the present invention comprises:

a first supporting member;

an outer guide pipe for penetrating a pedicle and creating a pathway into a vertebra, through which the first supporting member is to enter the vertebra; and an optional second supporting member to enter the vertebra through the outer guide pipe;

wherein the first and second supporting members each comprise an upper surface and a lower surface, the upper surfaces each having a first guide portion and a first engaging portion, and the lower surfaces each having a second guide portion and a second engaging portion, wherein the first guide portion corresponds in position to the second guide portion, wherein the first engaging portion corresponds in position to the second engaging portion, and wherein the second guide portion of the first supporting member extends, along a first axis, to form an extending portion which is arranged to be disposed in the outer guide pipe and to which the first guide portion of the second supporting member is slidably coupled, along the first axis, within the outer guide pipe, such that the second supporting member moves slidably into the vertebra and toward the first supporting member, along the first axis, and the first engaging portion of the second supporting member is engaged with the second engaging portion of the first supporting member.

In some embodiments, the first supporting member and the second supporting member each comprise a hollow-cored portion which has at least one opening disposed on a lateral side of the hollow-cored portion so that bone tissue of the vertebra grows into the first and second supporting members.

In some embodiments, the hollow-cored portions of the first supporting member and the second supporting member are each filled with an autograft bone, an allograft bone, or a synthetic bone graft substitute.

In some embodiments, a screw hole is disposed on a lateral side of the first supporting member and the second supporting member each and coupled to an inner guide pipe so as to drive the first supporting member and the second supporting member to slide within the outer guide pipe.

In some embodiments, the first guide portion comprises a recess, the second guide portion comprises a rib, and the extending portion is an extending shaft extended from the rib.

In some embodiments, the recess of the first guide portion comprises an open end to allow the rib of the second guide portion to enter it and a closed end for blocking the rib of the second guide portion.

The present invention further provides a method for introducing an intra-vertebral implant into a vertebrate of a subject in need thereof by using one or more supporting members as described herein.

Specifically, the method of the present invention comprises the steps of:

(a) introducing a first supporting member into a vertebra through a pedicle in a subject;

(b) optionally pushing the first supporting member in the vertebra, upward or downward;

(c) optionally and subsequently introducing the second supporting member into the vertebra through the pedicle, including slidably coupling the first guide portion of the second supporting member to the extending portion of the first supporting member and moving the second supporting member toward the first supporting member, along the first axis, such that the first engaging portion of the second supporting member is engaged with the second engaging portion of the first supporting member, leaving an excess part of the extending portion of the first supporting member exposing out of the first supporting member; and (d) optionally, cutting off the excess part of the extending portion of the second supporting member.

By using the one or more supporting members as described herein, the method of the present invention is effective in caudal-cranial expanding of the vertebra.

Fine technical features and preferred embodiments of the present invention are depicted by the accompanying drawings and described below so that persons skilled in the art can gain insight into the technical features of the present invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE EMBODIMENTS

Unless otherwise defined herein, every technical or scientific term used herein has the same meaning as generally understood by persons skilled in the art pertaining to the present invention.

Unless otherwise specified herein, the words "a" and "an" used herein mean "at least one."

Figure 1:
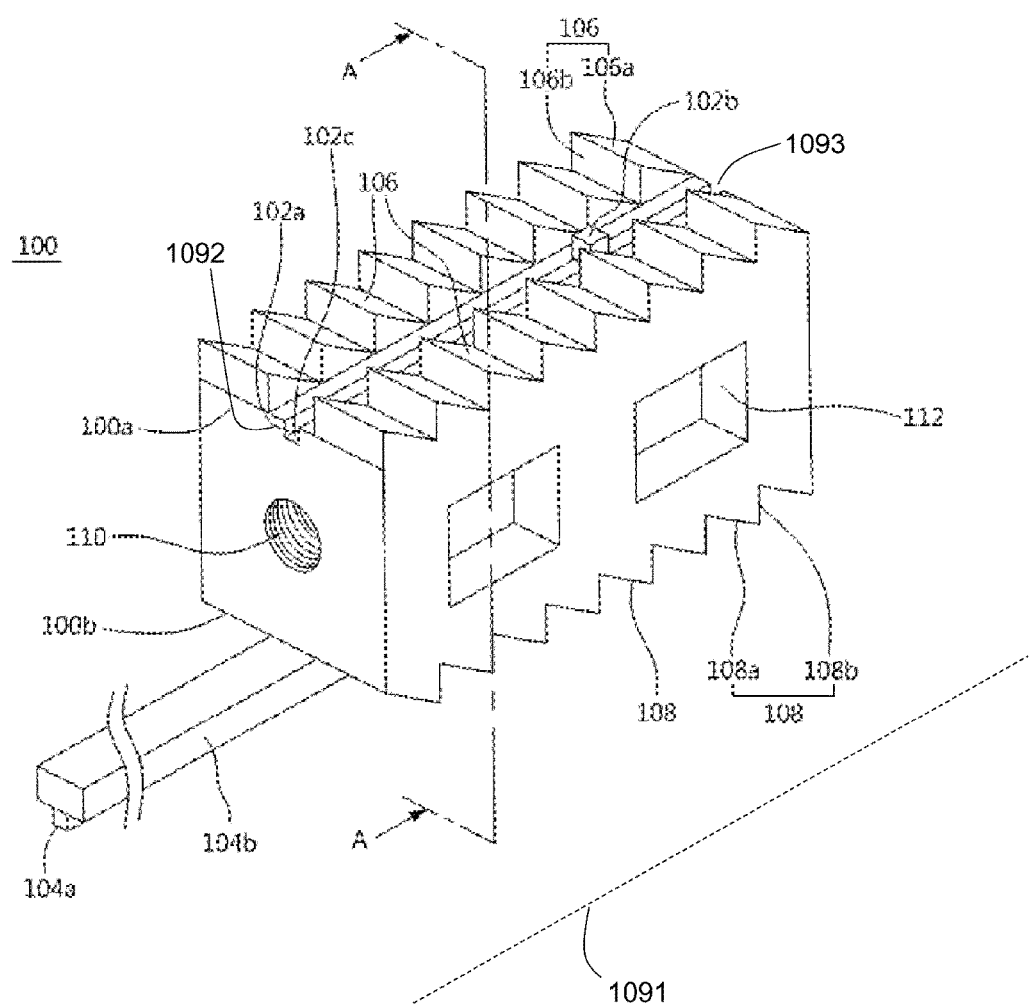
FIG. 1 is a perspective view of a supporting member for implanting into a vertebra according to the present invention, showing that the supporting member displays mirror symmetry about the transverse plane.
Figure 2:
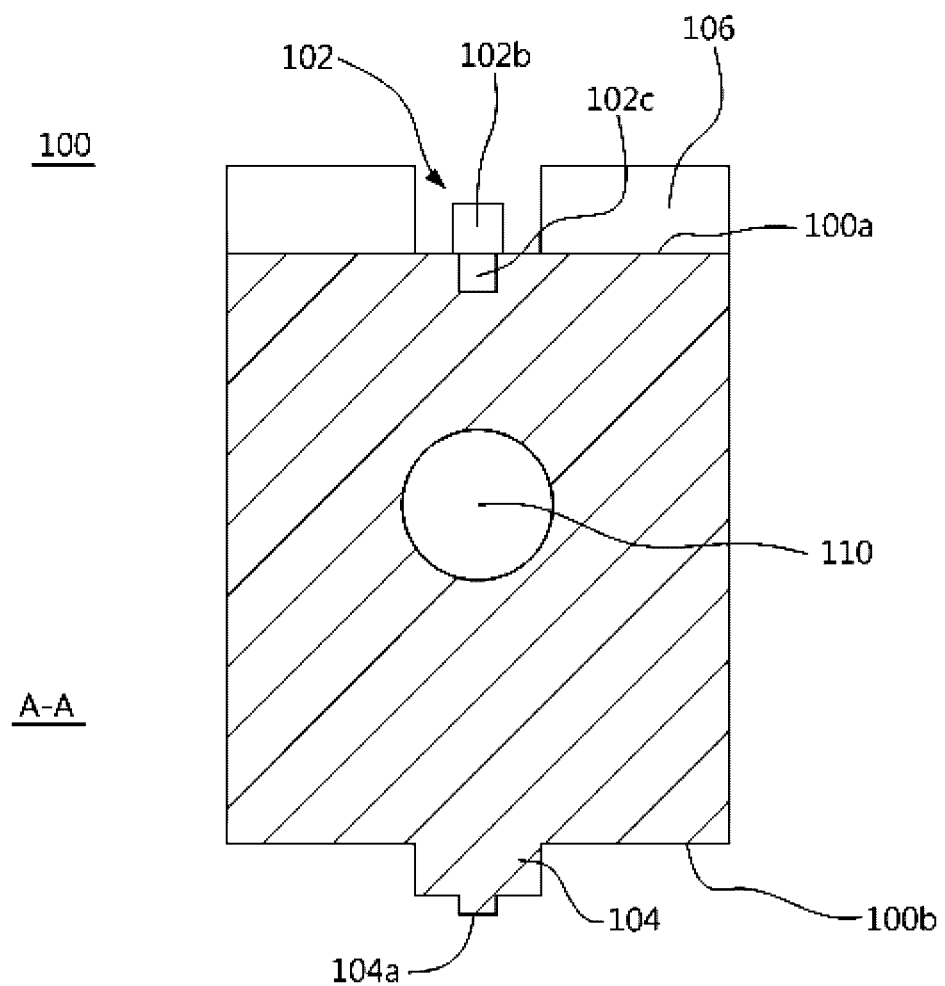
FIG. 2 is a cross-sectional view of the supporting member in the vertebra according to the present invention.

Referring to FIG. 1 and FIG. 2, there are shown a perspective view and a cross-sectional view of a supporting member for implanting into a vertebra according to the present invention. FIG. 2 is a cross-sectional view taken along line AA' of FIG. 1. A supporting member 100 comprises an upper surface 100a and a lower surface 100b. Specifically, an upper surface 100a is parallel to a lower surface 100b. A first guide portion 102 is, for example, a recess formed on the upper surface 100a. A first guide portion 102 comprises a first proximal end 1092 extending to a first distal end 1093 along a first axis 1091. A second guide portion 104 is, for example, a rib formed on the lower surface 100b and corresponding in shape to the recess of the first guide portion 102. A second guide portion 104 extends outward from the hollow-cored portion, along a first axis 1091, to form an extending portion, to which another supporting member is slidably coupled along a first axis 1091. A first engaging portion 106 comprises a plurality of teeth formed on the upper surface 100a. The first engaging portion 106 is formed along the two sides of the first guide portion 102. The teeth each comprise a first ramp 106a and a second ramp 106b with a steeper slope than the first ramp 106a. A second engaging portion 108 comprises a plurality of teeth formed on the lower surface 100b. The second engaging portion 108 is formed along the two sides of the second guide portion 104. The teeth each comprise a third ramp 108a and a fourth ramp 108b with a steeper slope than the third ramp 108a. The supporting member 100 comprises a hollow-cored portion which has a screw hole formed on a lateral side of the hollow-cored portion and between the upper and lower surfaces of the hollow-cored portion, and has a plurality of openings 112 formed on one or more lateral sides of the hollow-cored portion and between the upper and lower surfaces of the hollow-cored portion. The openings 112 are in communication with the hollow-cored portion of the supporting member 100. The hollow-cored portion of the supporting member 100 can be filled with an autograft bone, an allograft bone, or a synthetic bone graft substitute. After being implanted in a vertebra, the supporting member 100 integrates into its surrounding bone and thereby promotes fracture healing. In some embodiments, the hollow-cored portion is in a cubic shape.

The rib of the second guide portion 104 extends out of the hollow-cored portion of the supporting member 100, along a first axis 1091, to form an extending shaft 104b, to which another supporting member can be slidably coupled, along the first axis. A minor rib 104a is formed on a lateral surface of the rib of the second guide portion 104 and the extending shaft 104b, positioned distal to the hollow-cored portion of the supporting member 100. The recess of the first guide portion 102 comprises an open end 102a which is, from a lateral surface of the supporting member 100, in communication with the outside and extending to a closed end 102b that is opposite to the open end, along a first axis 1091, to define the limit of the displacement of the rib of the second guide portion 104. A minor recess 102c corresponding in position to the minor rib 104a of the rib of the second guide portion 104 is formed in the recess of the first guide portion 102. The minor recess 102c is horizontally inserted into the supporting member 100 and corresponds in position to the closed end 102b to form a fixing concave portion. The minor rib 104a protrudes slightly from one side of the rib of the second guide portion 104 to form a fixing convex portion which enters the fixing concave portion. When the minor rib 104a of a supporting member 100 enters the fixing concave portion of another supporting member 100, the first ramp 106a of a supporting member 100 abuts against the third ramp 108a of the other supporting member. The second ramp 106b of a supporting member 100 abuts against the fourth ramp 108b of the other supporting member.

In practice, multiple supporting members 100 are implanted one by one into a vertebra with a guide apparatus and combined inside the vertebra. After a first supporting member 100 has been implanted, the extending shaft 104b of the second guide portion 104 is extended outward, and then the recess of the first guide portion 102 of a second (the next) supporting member 100 gets slidably coupled to the extending shaft 104b of the second guide portion 104 of the first supporting member 100 and the second supporting member 100 slides toward the first supporting member 100, thereby allowing the first and second supporting members 100 to be combined inside the vertebra in a precise manner. After the first and second supporting members 100 have been precisely combined, the extending shaft 104b of the second guide portion 104 of the first supporting member 100 is trimmed by removing the excess part. By analogy, more said supporting members 100 (for example, the third, fourth, and . . . supporting members 100) can be implanted in the aforesaid manner.

The supporting members 100 are made of a metal, a polymer plastic, a ceramic material, or a biodegradable material. The metal is, for example, stainless steel, cobalt-chromium-molybdenum alloy, titanium, or titanium alloy. The polymer plastic is, for example, polyetheretherketone (PEEK), ultra-high molecular weight polyethylene (UHMWPE), polymethylmethacrylate (PMMA), or silicone rubber. The ceramic material is, for example, aluminum oxide, calcium phosphate salt, or biomedical glass. The biodegradable material is, for example, polydioxanone, poly(ε-caprolactone), polyanhydride, poly(ortho ester), copoly (ether-ester), polyamide, polylactone, poly(propylene fumarate), poly(lactic acid), poly(glycolyic acid), poly(lactide-co-glycolide), or a combination thereof.

Figure 3:
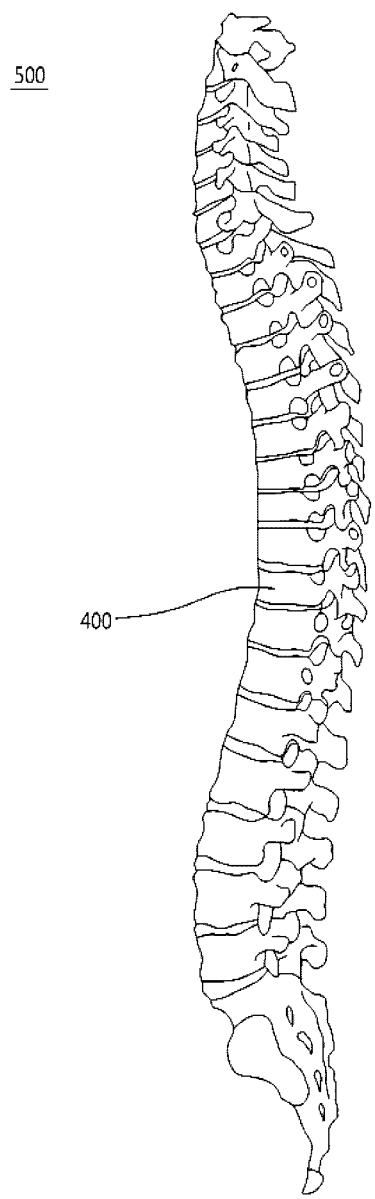
FIG. 3 is a schematic view of a vertebral column.

Referring to FIG. 3, a vertebral column (also known as spine) 500 comprises a plurality of vertebrae 400, and one of the vertebrae 400 has collapsed.

Figure 4:
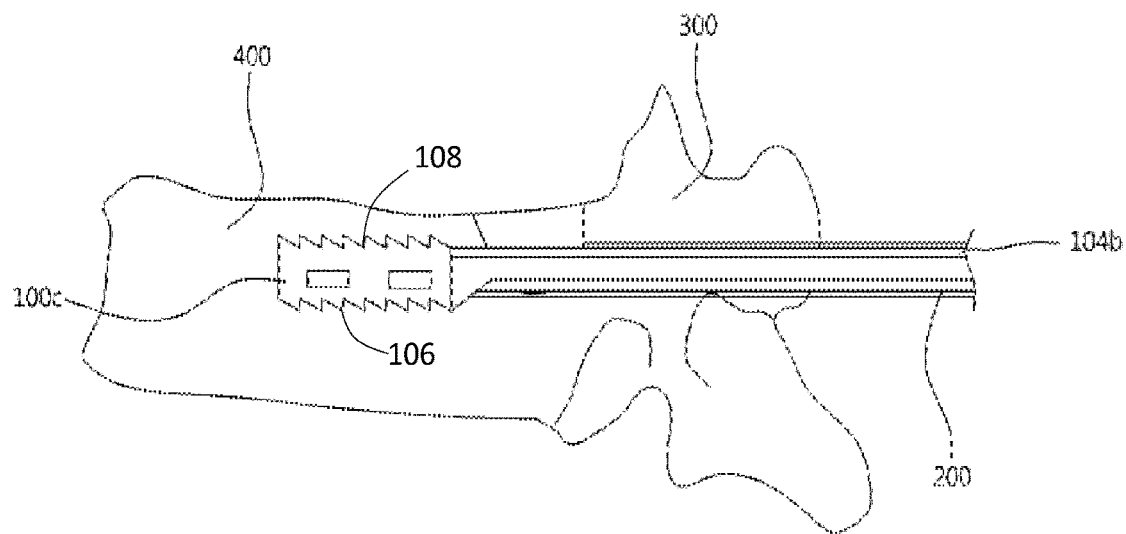
FIG. 4 is a schematic view of how to implant a supporting member into a vertebra with an implanting system according to the present invention.
Figure 5:
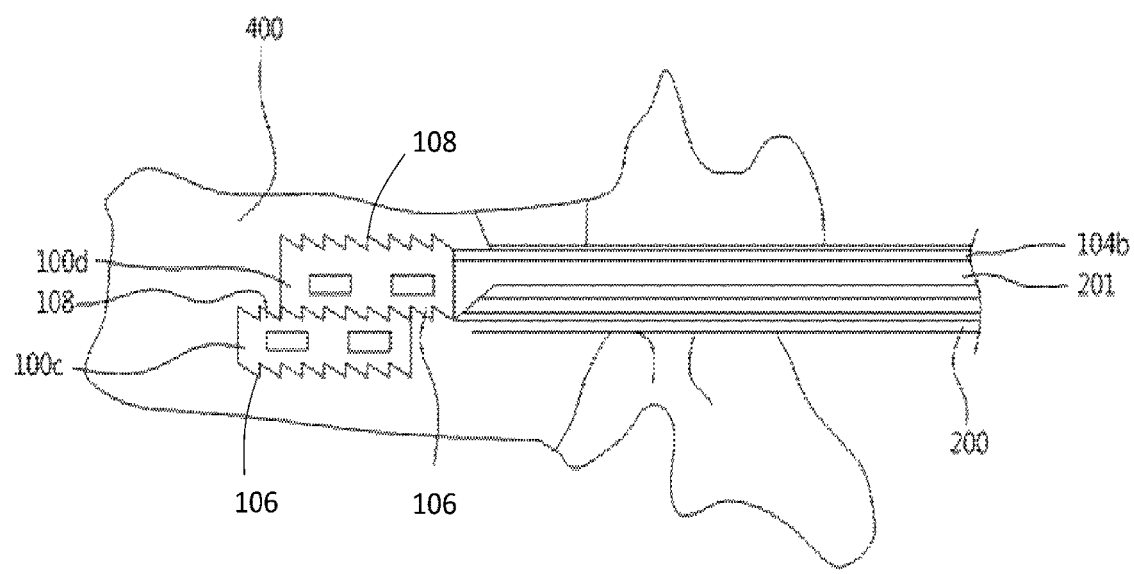
FIG. 5 is a schematic view of how to implant a supporting member into a vertebra with an implanting system according to the present invention.
Figure 6:
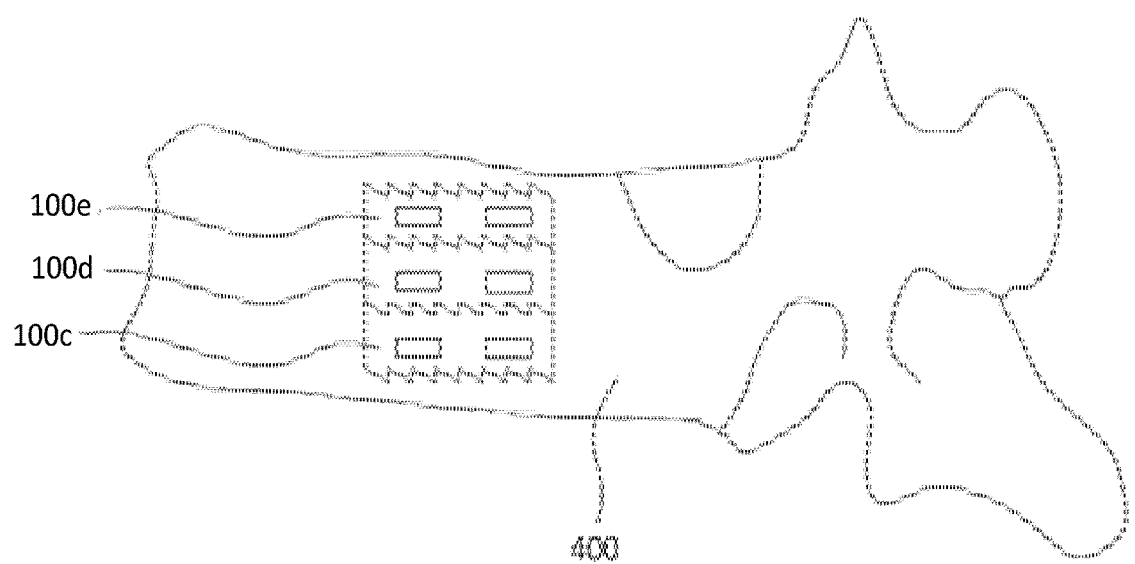
FIG. 6 is a schematic view of how to implant a supporting member into a vertebra with an implanting system according to the present invention.

Referring to FIG. 4 through FIG. 6, there are shown schematic views of how to implant a supporting member into a vertebra using an implanting system according to the present invention.

Referring to FIG. 4, an outer guide pipe 200 penetrates a pedicle 300 and enters the collapsed vertebra 400. The manner of introducing the outer guide pipe 200 into the collapsed vertebra 400 involves piercing the pedicle 300 with a hollow bone puncture needle (not shown) guided by x-ray imaging whereby the bone puncture needle enters the collapsed vertebrate, inserting a guide steel needle (not shown) along the bone puncture needle whereby the guide steel needle enters inside the vertebra 400, pulling out the bone puncture needle, and finally inserting the outer guide pipe 200 along the guide steel needle whereby the outer guide pipe enters inside the vertebra 400. Afterward, with the outer guide pipe 200 in place, a first supporting member 100c (through a screw hole (not shown) thereof) is coupled to an inner guide pipe 201. A medical professional pushes and moves, with the inner guide pipe 201, the first supporting member 100c from the outer guide pipe 200 sliding into the vertebra 400 and then removes the inner guide pipe 201 from the first supporting member 100c. At this point in time, the extending shaft 104b, which extends from the rib of the second guide portion 104 of the first supporting member 100c, is right inside the outer guide pipe 200.

Referring to FIG. 5, after a second supporting member 100d (through a screw hole (not shown) thereof) is coupled to an inner guide pipe 201, a first guide portion (not shown) of the second supporting member 100d is slidably coupled to an extension to the second guide portion 104 of the first supporting member 100c and thereby slides through the outer guide pipe 200 into the vertebra 400 while pushing and moving the first supporting member 100c downward or upward slightly (caudal-cranial expanding). When the second supporting member 100d moves into the vertebra 400, the teeth of the first engaging portion 106 of the second supporting member 100d mesh with the teeth of the second engaging portion 108 of the first supporting member 100c. As indicated by the aforesaid description of the structural features of the teeth, the second supporting member 100d can be smoothly pushed into the vertebra 400 but is prevented from being pulled out because of the structural features of the teeth. Therefore, the first engaging portion 106 of the second supporting member 100d becomes engaged with the second engaging portion 108 of the first supporting member 100c while the first guide portion of the second supporting member gets slidably coupled to the second guide portion of the first supporting member. After the second supporting member 100d and the first supporting member 100c have been combined and fixed in place, the medical professional can slide a hollow cutting apparatus along the second guide portion 104 of the first supporting member 100c until it reaches to the surface of the hollow-cored portion of the first supporting member 100c from which the second guide portion extends outward, trim the excess of the second guide portion 104 and remove it. Then, the inner guide pipe 201 can be pulled out of the second supporting member 100d. At this moment in time, the extension to the rib of the second guide portion 104 of the second supporting member 100d is right inside the outer guide pipe 200. In a specific embodiment, a supporting member implanted in a vertebra partially restores the collapsed vertebra to its normal condition; hence, more supporting members can be introduced into the partially restored vertebra to boost the support provided thereto until the vertebra is fully restored to its normal condition. Advantageously, the smallest wound is made to the collapsed vertebra in order to introduce one tiny supporting member into the vertebra and then introduce additional supporting members into the vertebra without the need to enlarge the wound, thereby providing full support to the vertebra.

Referring to FIG. 6, the medical professional implants a third supporting member 100e into the vertebra 400 by following the aforesaid steps. The first supporting member 100c, the second supporting member 100d, and the third supporting member 100e are combined to form a supporting framework as disclosed in the present invention with a view to supporting the collapsed vertebra 400. However, the present invention is not limited to the foresaid supporting framework composed of three supporting members; instead, according to the present invention, an appropriate number of aforesaid supporting members can be implanted in the collapsed vertebra 400 as needed.

According to the present invention, the supporting members are implanted in a collapsed vertebra one by one. The supporting members thus implanted in the vertebra are combined. Therefore, an appropriate number of tiny supporting members can be conveniently implanted in the collapsed vertebra as needed. Furthermore, an implanting system of the present invention enables a succeeding supporting member to be introduced into a collapsed vertebra while being guided by an extending shaft of a preceding supporting member and then coupled to the preceding supporting member accurately, allows the supporting members to be fixed in place as a result of their advancements, and ensures that the supporting members advance rather than retreat. Therefore, a supporting member for implanting into a vertebra and an implanting system using the supporting member according to the present invention overcome drawbacks of the prior art (for example, implanting a single filler into a collapsed vertebra comes with the likelihood of injuring peripheral nerves while the single filler is penetrating the pedicle of the vertebra, and implanting a single filler of a wrong size into a collapsed vertebra provides no support thereto.)

The present invention provides a supporting member for implanting into a vertebra of a subject, including: a hollow body including an upper surface and a lower surface opposite the upper surface; a first guiding part formed on the upper surface; a second guiding part corresponding to the first guiding part and formed on the lower surface; a first engaging part formed on the upper surface; and a second engaging part corresponding to the first engaging part and formed on the lower surface; wherein the second guiding part extends out an extending part from a side of the hollow body, and the extending part is configured to be slidably coupled to a first guiding part of another supporting member sliding to the lower surface of the supporting member, as a result two supporting members are slidably coupled to each other and engaged to each other. According to the invention, one single supporting member can be implanted into a vertebra of a subject, or two or more supporting members can be in sequence introduced into a vertebra of a subject and combined together therein.

In conclusion, the supporting member and system and method thereof of the present invention have advantages as follows:

1. A single supporting member can be small enough to penetrate the pedicle of a collapsed vertebra safely and thereby get implanted in the collapsed vertebra without injuring the pedicle or peripheral nerves.

2. Supporting members thus implanted in the compact, collapsed vertebra can be combined with a view to restoring the collapsed vertebra to its normal condition; the required number of the implanted supporting members depends on the height of the vertebra to be restored; and, theoretically speaking, the supporting members can be implanted as many as required to fill a collapsed vertebra.

3. During their combining process, the supporting members are unidirectionally tightened and thus are unlikely to loosen later.

4. The hollow-cored portion of each supporting member is conducive to dense inward growth of bone tissue.

5. The supporting members are made of a metal, a polymer plastic, or a biodegradable material and thereby possess mechanical properties required to resist pressure, tensile force, and torsional stress.

6. Modular, caudal-cranial expanding and intra-vertebral can be accomplished to support the vertebra and repair collapsed vertebra.

It is always true that the description of the present invention herein allows persons skilled in the art to make maximum use of the present invention without requiring any further explanation. Therefore, the description of the present invention herein and the appended claims are deemed illustrative, rather than restrictive in any way, of the scope of the present invention.

SYMBOLS 100 supporting member
100c a first supporting member
100d a second supporting member
100e a third supporting member 100a an upper surface
100b a lower surface
102 first guide portion
102a an open end
102b a closed end
102c a minor recess
104 a second guide portion
104a a minor rib
104b a extending shaft
106 a first engaging portion
106a a first ramp
106b a second ramp
108 a second engaging portion
108a a third ramp
108b a fourth ramp
110 a screw hole
112 openings
1091 a first axis
1092 a first proximal end
1093 a second distal end
400 a vertebra
500 a vertebral column (also known as spine)
300 pedicle
200 an outer guide pipe
201 an inner guide pipe

What is claimed is:

1. A combinable supporting member that is adapted to be implanted into a vertebra, comprising:
    a hollow-cored portion having an upper surface and a lower surface opposing the upper surface;
    a first guide portion formed on the upper surface;
    a second guide portion corresponding in position to the first guide portion and formed on the lower surface;
    a first engaging portion formed on the upper surface; and
    a second engaging portion corresponding in position to the first engaging portion and formed on the lower surface,
    wherein the second guide portion extends outward from the hollow-cored portion, along a first axis, to form an extending portion, to which another supporting member is slidably coupled along the first axis.

2. The supporting member of claim 1, wherein the hollow-cored portion is in a cubic shape.

3. The supporting member of claim 1, wherein at least one opening is disposed on a lateral side of the hollow-cored portion.

4. The supporting member of claim 1, wherein a screw hole is disposed on a lateral side of the hollow-cored portion.

5. The supporting member of claim 1, wherein the first guide portion comprises a first proximal end extending to a first distal end along the first axis.

6. The supporting member of claim 1, wherein the first guide portion comprises a recess that comprises a first proximal end extending to a distal end along the first axis, and the second guide portion comprises a rib extending outward from a lateral surface of the hollow-cored portion of the supporting member, along the first axis, to form an extending shaft as the extending portion.

7. The supporting member of claim 1, wherein the first guide portion comprises a recess that comprises an open end in communication with an outside environment of the supporting member, extending to a closed end that is opposite to the open end along the first axis.

8. The supporting member of claim 1, wherein the first engaging portion is formed on two sides of the first guide portion, and the second engaging portion is formed on two sides of the second guide portion.

9. The supporting member of claim 1, wherein the first engaging portion comprises a plurality of teeth each comprising a first oblique surface and a second oblique surface with a steeper slope than the first oblique surface, and the second engaging portion comprises a plurality of teeth each comprising a third oblique surface and a fourth oblique surface with a steeper slope than the third oblique surface.

10. The supporting member of claim 1, wherein the supporting member is made of a metal, a polymer plastic, or a biodegradable material.

11. An intra-vertebral implanting system or kit, comprising:
    a first supporting member;
    an outer guide pipe for penetrating a pedicle and creating a pathway into a vertebra, through which the first supporting member is to enter the vertebra; and
    a second supporting member to enter the vertebra through the outer guide pipe;
    wherein the first and second supporting members each comprise an upper surface and a lower surface, the upper surfaces each having a first guide portion and a first engaging portion, and the lower surfaces each having a second guide portion and a second engaging portion,
    wherein the first guide portion corresponds in position to the second guide portion,
    wherein the first engaging portion corresponds in position to the second engaging portion, and
    wherein the second guide portion of the first supporting member extends, along a first axis, to form an extending portion which is arranged to be disposed in the outer guide pipe and to which the first guide portion of the second supporting member is slidably coupled, along the first axis, within the outer guide pipe, such that the second supporting member moves slidably into the vertebra and toward the first supporting member, along the first axis, and the first engaging portion of the second supporting member is engaged with the second engaging portion of the first supporting member.

12. The implanting system of claim 11, wherein the first supporting member and the second supporting member each comprise a hollow-cored portion which has at least one opening disposed on a lateral side of the hollow-cored portion so that bone tissue of the vertebra grows into the first and second supporting members.

13. The implanting system of claim 12, wherein the hollow-cored portions of the first supporting member and the second supporting member are each filled with an autograft bone, an allograft bone, or a synthetic bone graft substitute.

14. The implanting system of claim 11, wherein a screw hole is disposed on a lateral side of the first supporting member and the second supporting member each and coupled to an inner guide pipe so as to drive the first supporting member and the second supporting member to slide within the outer guide pipe.

15. The implanting system of claim 11, wherein the first guide portion comprises a recess, the second guide portion comprises a rib, and the extending portion is an extending shaft extended from the rib.

16. The implanting system of claim 15, wherein the recess of the first guide portion comprises an open end to allow the rib of the second guide portion to enter it and a closed end for blocking the rib of the second guide portion.

17. The implanting system of claim 11, wherein the first engaging portion comprises a plurality of teeth each comprising a first oblique surface and a second oblique surface with a steeper slope than the first oblique surface, and the second engaging portion comprises a plurality of teeth each comprising a third oblique surface and a fourth oblique surface with a steeper slope than the third oblique surface.

18. A method for introducing an intra-vertebral implant into a vertebra of a subject in need,
   wherein the implant comprises a first supporting member and a second supporting member, said first and second supporting members each comprising an upper surface and a lower surface, the upper surfaces each having a first guide portion and a first engaging portion, and the lower surfaces each having a second guide portion and a second engaging portion, said first guide portion corresponding in position to the second guide portion, and said first engaging portion corresponding in position to the second engaging portion, and
   wherein the second guide portion of the first supporting member extends, along a first axis, to form an extending portion,
   said method comprising the steps of:
      (a) introducing the first supporting member into the vertebra through a pedicle,
      (b) pushing the first supporting member in the vertebra, upward or downward;
      (c) subsequently introducing the second supporting member into the vertebra through the pedicle, including slidably coupling the first guide portion of the second supporting member to the extending portion of the first supporting member and moving the second supporting member toward the first supporting member, along the first axis, such that the first engaging portion of the second supporting member is engaged with the second engaging portion of the first supporting member, leaving an excess part of the extending portion of the first supporting member exposing out of the first supporting member; and
      (b) cutting off the excess part of the extending portion of the second supporting member.

19. The method of claim 18, wherein the first guide portion comprises a recess, the second guide portion comprises a rib, and the extending portion is an extending shaft extended from the rib.

20. The method of claim 18, wherein the method is effective in caudal-cranial expanding of the vertebra.

* * * * *